United States Patent [19]

Tang et al.

[11] Patent Number: 4,581,179

[45] Date of Patent: Apr. 8, 1986

[54] PROCESS FOR THE PREPARATION OF TRIFLUOROMETHYLBENZOYL CHLORIDES AND BROMIDES FROM TRIFLUOROMETHYLBENZOYL FLUORIDES

[75] Inventors: David Y. Tang, Amherst; Byron R. Cotter, Grand Island, both of N.Y.

[73] Assignee: Occidental Chemical Corporation, Niagara Falls, N.Y.

[21] Appl. No.: 140,893

[22] Filed: Apr. 16, 1980

[51] Int. Cl.$^4$ ............................................. C07C 51/58
[52] U.S. Cl. ............................................. 260/544 D
[58] Field of Search ......................... 260/544 D, 544 Y

[56] References Cited

U.S. PATENT DOCUMENTS

| | | | |
|---|---|---|---|
| 3,449,416 | 6/1969 | Brotherton | 260/544 Y |
| 4,079,089 | 3/1978 | Klauke . | |
| 4,079,090 | 3/1978 | Buttner et al. . | |
| 4,080,378 | 3/1978 | Zoche et al. | 260/544 D |
| 4,093,669 | 6/1978 | Klauke . | |

OTHER PUBLICATIONS

Patai, Saul, *The Chemistry of Acyl Halides* (1972), pp. 52-53, Interscience Publ.
Olah, G. A. et al., *The Journal of Organic Chemistry*, vol. 26 (1961), pp. 237-238.
Lichtenberger, Jean et al., *Bull. Soc. Chim.* (1962), pp. 915-919 of Memoires.
Yagupol'skil, L. M. et al., *J. Gen. Chemistry, USSR*, vol. 31, (1961), pp. 845 and 848.
Stogryn, Eugene L., *J. Medicinal Chemistry*, vol. 16 (1973), pp. 1399-1401.

*Primary Examiner*—Natalie Trousof
*Assistant Examiner*—L. Hendriksen
*Attorney, Agent, or Firm*—James F. Tao; Arthur S. Cookfair

[57] ABSTRACT

Trifluoromethylbenzoyl chlorides or bromides are prepared by contacting trichloromethylbenzoyl chlorides or tribromomethylbenzoyl bromides with trifluoromethylbenzoyl fluorides in the presence of a halogen transfer catalyst.

19 Claims, No Drawings

PROCESS FOR THE PREPARATION OF TRIFLUOROMETHYLBENZOYL CHLORIDES AND BROMIDES FROM TRIFLUOROMETHYLBENZOYL FLUORIDES

BACKGROUND OF THE INVENTION

This invention relates to a process for the preparation of trifluoromethylbenzoyl chlorides and trifluoromethylbenzoyl bromides. The products are useful intermediates for the production of various dyestuffs and agricultural chemical products.

Various methods are known for the preparation of trifluoromethylbenzoyl halides. It is known, for example, to prepare trifluoromethylbenzoyl chloride by reaction of trifluoromethylbenzoic acid with thionyl chloride. The starting material for such reaction, trifluoromethylbenzoic acid may be prepared by several methods, each of which is a multi-stepped process involving relatively expensive starting materials and/or intermediates. Thus, for example, it is known to prepare trifluoromethylbenzoic acid by cyanation of bromobenzotrifluoride and hydrolysis of the resulting cyanobenzotrifluoride. In another known method, bromobenzotrifluoride is reacted with magnesium and the resultant Grignard reagent is reacted with carbon dioxide to form trifluoromethylbenzoic acid.

In still another method xylene may be oxidized to toluic acid, the acid group esterified, and the methyl group chlorinated and then fluorinated to yield trifluoromethylbenzoic acid.

Although the processes of the prior art are useful for the preparation of trifluoromethylbenzoyl chloride, it will be appreciated that improvements in the efficiency, economy of preparation and yield of the desired product are nevertheless desirable.

In co-pending application Ser. No. 140,894, filed Apr. 16, 1980, now U.S. Pat. No. 4,500,471, an improved process for the preparation of trifluoromethylbenzoyl chlorides and bromides is disclosed. The process disclosed therein comprises the preparation of trifluoromethylbenzoyl chlorides or bromides by reaction of trichloromethylbenzoyl chlorides or tribromomethylbenzoyl bromides with hydrogen fluoride in the presence of a halogen transfer catalyst. In addition to the desired trifluoromethylbenzoyl chloride or bromide, the reaction product may contain varying amounts of over-fluorinated product, in particular, trifluoromethylbenzoyl fluoride, and various mixed fluoro-bromo or fluorochloro products such as chlorodifluoromethylbenzoyl chloride and the like. The production of such over- or partially fluorinated by-products, even in minor amounts, is economically unattractive and may present additional problems with respect to the proper disposal thereof. It will be appreciated that a simple, economical method for the conversion of such products to the desired trifluoromethylbenzoyl chlorie or bromide product would be particularly useful to avoid the aforementioned economic and disposal problems.

Accordingly, it is an object of the present invention to provide a simple, direct method for the conversion of trihalomethylbenzoyl halide mixtures to trifluoromethylbenzoyl chlorides or bromides. It is a further object to provide a halogen exchange process for the conversion of trifluoromethylbenzoyl fluorides to trifluoromethylbenzoyl chlorides or bromides.

SUMMARY OF THE INVENTION

It has now been found that trifluoromethylbenzoyl chlorides or bromides can be prepared by halogen exchange process which comprises contacting trihalomethylbenzoyl halides of the formula

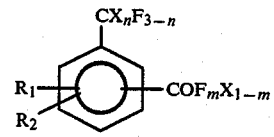

wherein X is chlorine or bromine, n is 0 to 2, m is 0 or 1 and $R_1$ and $R_2$ are independently selected from the group consisting of hydrogen, fluorine, chlorine, bromine, alkyl, aryl, haloaryl, alkoxy, fluoroalkoxy, aryloxy, haloaryloxy, nitro, cyano, sulfonyl, and carboxylic acid chloride, with trihalobenzoyl halides of the formula

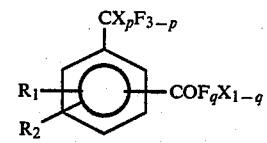

wherein p is 1 to 3, q is 0 or 1, and X, $R_1$ and $R_2$ are as defined above, in the presence of a halogen transfer catalyst.

The preferred alkyl, alkoxy and fluoroalkoxy groups represented by $R_1$ and $R_2$ are those of one to six carbon atoms, and most preferably methyl, methoxy, and fluoromethoxy groups. The preferred aryl and aryloxy groups are phenyl and phenoxy or substituted phenyl and phenoxy groups wherein substituents such as chloro-, fluoro-, bromo-, nitro-, cyano-, methyl-, or carboxylic acid chloride are present on the ring. The most preferred trihalobenzoyl halide reactants are those of the above formula wherein $R_2$ is hydrogen and $R_1$ is hydrogen, fluorine, chlorine, bromine, nitro, cyano, or methyl.

In the process of the invention the halogen exchange of fluorine with chlorine or bromine atoms may occur on the intermolecular and/or intra-molecular level to result in the selective substitution of fluorine on the trihalomethyl group of the reactant and chlorine or bromine on the acid halide group.

DESCRIPTION OF PREFERRED EMBODIMENTS

In a preferred embodiment, the process of this invention comprises contacting trihalomethylbenzoyl halide of the formula

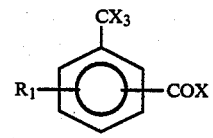

wherein X is chlorine or bromine, $R_1$ is hydrogen, fluorine, chlorine, bromine, nitro, cyano or methyl; and most preferably, the compound m-trichloromethylbenzoyl chloride or p-trichloromethylbenzoyl chloride with a corresponding substituted or unsubstituted trifluoromethylbenzoyl fluoride of the formula

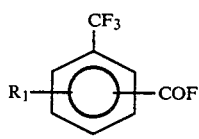

wherein $R_1$ is as defined hereinabove, in the presence of a halogen transfer catalyst to yield the corresponding substituted or unsubstituted trifluoromethylbenzoyl halide of the formula

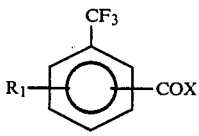

wherein X and $R_1$ are as defined hereinabove.

Under ideal stoichiometic conditions three moles of trifluoromethylbenzoyl fluoride are contacted with one mole of trichloromethylbenzoyl chloride or tribromomethylbenzoyl bromide in the presence of a halogen transfer catalyst to yield four moles of trifluoromethylbenzoyl chloride or bromide. It will be understood however, that greater or less than stoichiometric amounts of the reactants can be employed. Thus, in accordance with the process of this invention substituted or unsubstituted trichloromethylbenzoyl chloride or tribromomethylbenzoyl bromide may be reacted with corresponding substituted or unsubstituted trifluoromethylbenzoyl fluorides, in the presence of a halogen transfer catalyst to produce the corresponding substituted or unsubstituted trifluoromethylbenzoyl chloride or bromide.

The reaction in accordance with the invention is carried out in the presence of a halogen transfer catalyst. Such catalysts are well known in literature and include for example ferric chloride, aluminum chloride, molybdenum pentachloride, titanium tetrachloride, antimony pentafluoride, antimony pentachloride, antimony-V-chloride-fluoride, and the like. The preferred catalyst is antimony pentachloride. Typically, the catalyst is antimony pentachloride. Typically, the catalyst is employed in amounts of about 0.01 to about 10 percent by weight and preferably about 0.1 to about 3 percent by weight based on the weight of the reaction mixture.

The process of the invention may be carried out over a wide range of conditions. The process is preferably carried out at atmospheric pressure, however subatmospheric and superatmospheric pressures may be employed if desired. The temperature range under atmospheric conditions may vary between the melting point and the boiling point of the reaction mixture. Preferably however the reaction is carried out in a temperature range from about 0° to about 100° Celsius and most preferably from about 50° to about 80° Celsius.

Although it is preferred to carry out the reaction neat, a suitable inert solvent may be employed if desired. Suitable solvents include for example, nitrobenzene, carbon disulfide, and the like.

If desired, small amounts of hydrogen fluoride may be added during the halogen exchange process to provide additional fluorine atoms, especially when stoichiometry of the reaction mixture is such that the quantity of fluorine atoms is insufficient for the desired yield of trifluoromethylbenzoyl chloride or bromide. Such hydrogen fluoride addition may be carried out in accordance with the process disclosed in co-pending application Ser. No. 140,894, filed Apr. 16, 1980, now U.S. Pat. No. 4,500,471, the disclosure of which is incorporated herein by reference.

The following specific examples are provided to further illustrate the invention in a manner in which they be carried out. It will be understood, however, that the specific details given in the examples have been chosen for purposes of illustration and are not to be construed as a limitation on the invention. In the examples, unless otherwise indicated, all parts and percentages are by weight and all temperatures are in degrees Celsius.

EXAMPLE 1

A mixture of 2.3 parts of 3-trichloromethylbenzoyl chloride, 5.0 parts of 3-trifluoromethylbenzoyl fluoride, and 0.18 parts an antimony pentachloride was charged to a reaction vessel and heated to 75°–80° C. The mixture was maintained in that temperature range, with stirring, for about one hour, then cooled to room temperature and analyzed by gas chromatographic and mass spectroscopic techniques. The reaction product was found to contain about 22% 3-trifluoromethylbenzoyl fluoride; 56% 3-trifluoromethylbenzoyl chloride; 9% 3-trichloromethylbenzoyl chloride; and about 6% mixed fluoro-chloromethylbenzoyl halides.

EXAMPLE 2

A mixture of 2.9 parts of 4-trifluoromethylbenzoyl fluoride; 2.6 parts of 4-trichloromethylbenzoyl chloride and 0.04 parts of antimony pentachloride was charged to a reaction vessel and heated to about 55° C. The mixture was maintained at about that temperature, with stirring, for about six hours, then cooled to room temperature and analyzed by gas chromatographic and mass spectroscopic techniques. The reaction product was found to contain about 16.5% 4-trifluoromethylbenzoyl fluoride; 63.4% 4-trifluoromethylbenzoyl chloride; 15% mixed fluoro-chloromethylbenzoyl halides; 3.6% 4-trichloromethylbenzoyl chloride.

EXAMPLE 3

The procedure of Example 2 was repeated except that in place of the antimony pentachloride, there was substituted 0.04 parts of molybdenum pentachloride. Analysis of the reaction product by gas chromatography and mass spectroscopy indicated about 38% 4-trifluoromethylbenzoyl fluoride; 24% 4-trifluoromethylbenzoyl chloride; 18% mixed 4-trichloromethylbenzoyl halides; and 17% 4-trichloromethylbenzoyl chloride.

EXAMPLE 4

A mixture of 27 parts of 4-chlorodifluoromethylbenzoyl chloride, 23 parts of 4-dichlorofluoromethylbenzoyl fluoride, and 1.0 part of antimony pentachloride was charged to a reaction vessel and heated to about 55° C. The mixture was maintained at that temperature, with stirring, for about two hours, then cooled to room temperature. Analysis by gas chromatography and mass spectroscopy indicated a reaction product containing about 0.8% trifluoromethylbenzoyl fluoride; 39.7% trifluoromethylbenzoyl chloride; 36.3% chlorodifluoromethylbenzoyl chloride; 15.4% dichlorofluoromethylbenzoyl chloride; and 5.9% trichloromethylbenzoyl chloride.

EXAMPLE 5

The procedure of Example 4 was repeated except that in place of the 4-chlorodifluoromethylbenzoyl chloride and 4-dichloromethylbenzoyl fluoride there was substituted 42 parts of 4-trichloromethylbenzoyl fluoride and 8 parts of 4-dichlorofluoromethylbenzoyl fluoride. The reaction product consisted of about 2% 4-trifluoromethylbenzoyl fluoride; 12.3% 4-trifluoromethylbenzoyl chloride; 22.1% 4-chlorodifluoromethylbenzoyl chloride; 22.3% 4-dichlorofluoromethylbenzoyl chloride; and 38.3% 4-trichloromethylbenzoyl chloride.

When the general process of the foregoing examples is repeated except that brominated reactants, such as tribromomethylbenzoyl bromide or fluoride, dibromofluoromethylbenzoyl bromide or fluoride, and the like are employed in substitution for the chlorinated reactants of the examples, a product containing trifluoromethylbenzoyl bromide is obtained. Similarly where various substituted trihalomethylbenzoyl halides having nuclear substituents $R_1$ and $R_2$ as defined hereinabove, are employed, the correspondingly substituted trifluoromethylbenzoyl chlorides or bromides are obtained.

What is claimed is:

1. A process for the preparation of trifluoromethylbenzoyl halides of the formula

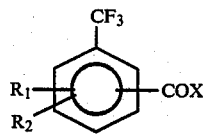

wherein X is chlorine or bromine and $R_1$ and $R_2$ are independently selected from the group consisting of hydrogen, fluorine, chlorine, bromine, alkyl, aryl, haloaryl, alkoxy, fluoroalkoxy, aryloxy, haloaryloxy, nitro, cyano, sulfonyl, and carboxylic acid chloride, which comprises contacting a compound of the formula

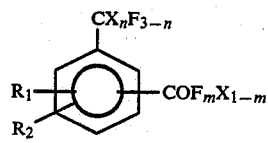

wherein n is 0 to 2, m is 0 or 1 provided that when n is 0, m is 1; and X, $R_1$ and $R_2$ are as defined above with a compound of the formula

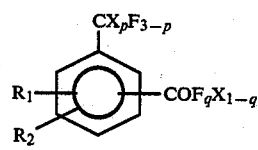

wherein p is 1–3, q is 0 or 1 and X, $R_2$ and $R_2$ are as defined above in the presence of a halogen transfer catalyst.

2. A process according to claim 1 wherein the process is carried out at about atmospheric pressure.

3. A process according to claim 2 wherein the process is carried out at a temperature of between about 0° Celsius and about 100° Celsius.

4. A process according to claim 1 wherein the halogen transfer catalyst is antimony pentachloride.

5. A process according to claim 1 wherein $R_2$ is hydrogen and $R_1$ is hydrogen, fluorine, chlorine, bromine, nitro, cyano or methyl.

6. A process according to claim 5 wherein the process is carried out at about atmospheric pressure and at a temperature of between about 0° Celsius and about 100° Celsius.

7. A process according to claim 6 wherein the halogen transfer catalyst is antimony pentachloride.

8. A process for the preparation of 4-trifluoromethylbenzoyl chloride which comprises contacting 4-trifluoromethylbenzoyl fluoride with 4-trichloromethylbenzoyl chloride in the presence of a halogen transfer catalyst.

9. A process according to claim 8 wherein the process is carried out at about atmospheric pressure.

10. A process according to claim 9 wherein the process is carried out at a temperature of between about 0° Celsius and about 100° Celsius.

11. A process according to claim 8 wherein the halogen transfer catalyst is antimony pentachloride.

12. A process for the preparation of 3-trifluoromethylbenzoyl chloride which comprises contacting 3-trifluoromethylbenzoyl fluoride with 3-trichloromethylbenzoyl chloride in the presence of a halogen transfer catalyst.

13. A process according to claim 12 wherein the process is carried out at about atmospheric pressure.

14. A process according to claim 13 wherein the process is carried out at a temperature of between about 0° Celsius and about 100° Celsius.

15. A process according to claim 12 wherein the halogen transfer catalyst is antimony pentachloride.

16. A process for the preparation of trifluoromethylbenzoyl chloride which comprises contacting a first compound of the formula

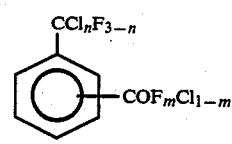

wherein n is 0 to 2 and m is 0 or 1, provided that when n is 0, m is 1, with a second compound of the formula

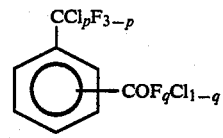

wherein p is 1 to 3 and q is 0 or 1 in the presence of a halogen transfer catalyst.

17. A process according to claim 16 wherein the process is carried out at about atmospheric pressure.

18. A process according to claim 17 wherein the process is carried out at a temperature of between about 0° Celsius and about 100° Celsius.

19. A process according to claim 16 wherein the halogen transfer catalyst is antimony pentachloride.

* * * * *